United States Patent [19]
Carter

[11] Patent Number: 5,938,646
[45] Date of Patent: Aug. 17, 1999

[54] MEDICAL UTILITY STORAGE ASSEMBLY FOR REUSABLE MEDICAL EQUIPMENT

[76] Inventor: Thomas E. Carter, 3423 West Kimber Dr., Newbury Park, Calif. 91302

[21] Appl. No.: 08/953,302

[22] Filed: Oct. 17, 1997

[51] Int. Cl.[6] .............................. A61M 1/00; B65D 90/04
[52] U.S. Cl. ......................... 604/317; 604/322; 604/410; 220/404; 220/524
[58] Field of Search ..................................... 604/317, 322, 604/408, 410; 220/419, 420, 404, 408, 908, 909, 524

[56] References Cited

U.S. PATENT DOCUMENTS

| | | |
|---|---|---|
| 3,575,225 | 4/1971 | Muheim . |
| 4,101,991 | 7/1978 | Sandonato ...................................... 5/90 |
| 4,874,103 | 10/1989 | Quisenberry et al. ....................... 220/1 |
| 5,022,548 | 6/1991 | Stakis .................................... 220/23.83 |
| 5,111,958 | 5/1992 | Witthoeft ................................ 220/408 |
| 5,148,940 | 9/1992 | Mendise ................................... 220/404 |

Primary Examiner—John G. Weiss
Assistant Examiner—David J. Cho
Attorney, Agent, or Firm—Price Gess & Ubell

[57] ABSTRACT

A medical storage assembly for reusable medical equipment includes a main storage bag having an opening, a bottom and an interconnecting wall which is operatively suspended from a mounting member that can be removably secured to a vertical support pole. A pivotable rigid lid member is connected to the mounting member and is configured to enable the closing of the opening of the medical storage bag. The medical storage bag can include a plurality of sub-storage bags that are removably mounted within the main storage bag and are removably connected together to provide open configurations whereby different types of reusable medical equipment can be stored. Alternatively, the main storage bag can hold used blood product containers and can be provided with an exterior compartment member of a configuration to hold medical forms that identify the recipient patient with the used blood product container.

18 Claims, 4 Drawing Sheets

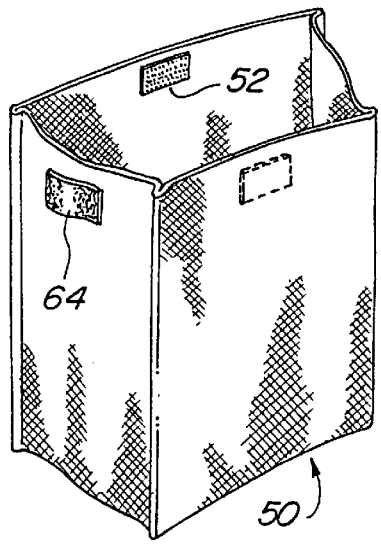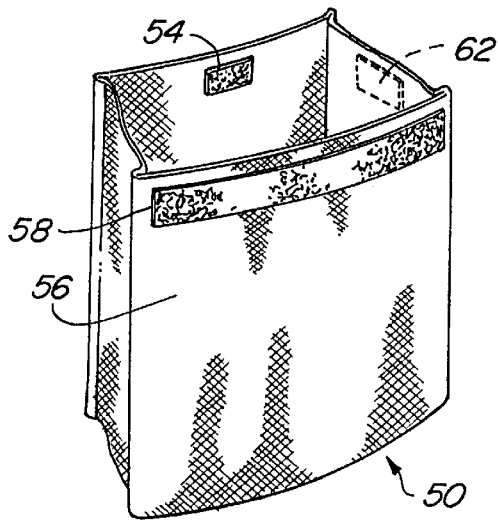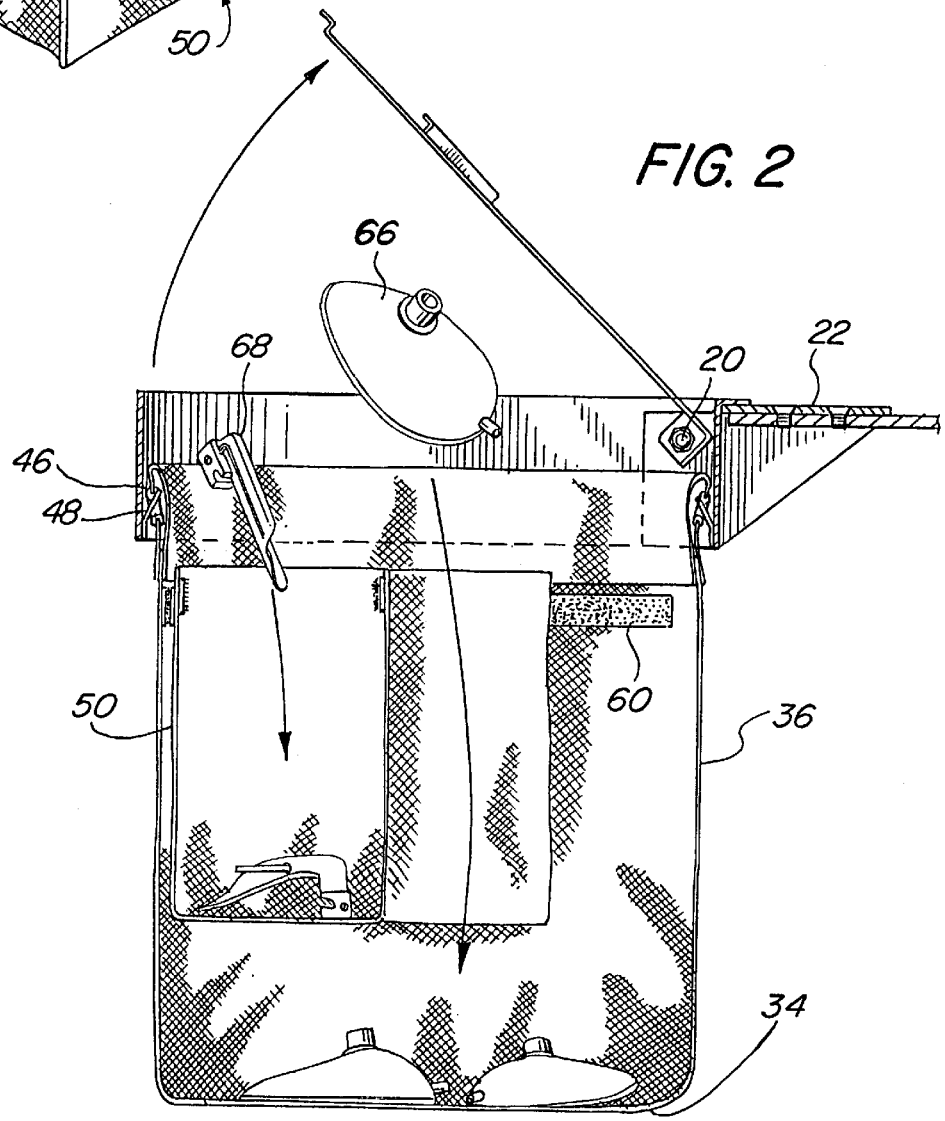

MEDICAL UTILITY STORAGE ASSEMBLY FOR REUSABLE MEDICAL EQUIPMENT

BACKGROUND OF THE INVENTION

1. Field of the Invention

The present invention is directed to a medical utility storage assembly that can be utilized in a hospital operating room for receiving and storing reusable medical equipment and more particularly to a rigid mounting member that can be mounted on a vertical support member for suspending a washable main storage bag mounting removable sub-storage bags to secure and store reusable medical equipment and supply items for subsequent cleaning, sterilization and recommissioning for use.

2. Description of Related Art

In operating rooms in surgical centers, hospitals and medical offices, various types of relatively expensive reusable medical equipment are utilized in an operation procedure. For example, anesthesia face masks are commonly used for a patient and they can be subsequently cleaned and sterilized for reuse. Another example of reusable equipment is a laryngoscope blade that can incorporate white halogen lamps. Laryngoscopes and other such reusable equipment and/or medical supplies are relatively expensive pieces of equipment that must be cleaned and sanitized for reuse.

Generally, operating rooms have not established an optimum protocol nor storage equipment for the securing of such medical items, their storage during and after the operation, and their transport from the operating room to another location where proper care can be given to refurbishing and sanitizing such medical equipment.

Usually, a medical operating room will include a utility hamper mounted on a wheeled cart for soiled sheets and other soiled drapes which are then transported to a utility linen closet for subsequent transportation to a laundry or to a transport truck and then to a commercial laundry. Also, a container or a support vessel lined with a "red" plastic bag is usually available for soiled/contaminated disposable plastic, paper and metal items that are utilized during an operation.

As a result, contaminated and reusable small medical equipment and supplies are frequently placed on any readily available surface within an arm's reach of the anesthesiologist, or other operating room surgical personnel, once the items have been used on the patient. As a result, these pieces of equipment and reusable plastic and metal medical supply items are sources of contamination and they are subject to being mistakenly discarded with other disposable metal, plastic and paper items at the end of the surgical procedure.

While it may be conceived that duplicating the utility hamper would be a potential solution for this prior art problem, the realities of the operation room are counter to this solution. There is a relatively cramped space with a significant amount of sophisticated equipment, hoses, lines and wires, surrounding the patient, in addition to intravenous (IV) poles with their attached IV pumps with various tubing extending from the pumps to the patient's arms and other IV sites. As can be appreciated, the anesthesia machine, the various monitoring equipment, surgical equipment, and so forth, make the addition of another wheeled device difficult to accommodate in a normal operating room. Additionally, if a second portable hamper on wheels was introduced, the same personnel may confuse this hamper with either the linen hamper or the contaminated refuse hamper, and the possibility of the destruction and discarding of expensive reusable medical items would further increase. The realities of a medical operating room are that the patient should be the prime focus of the attention of the doctors and support personnel and they should not be burdened with extraneous decision making responsibilities.

As a result, the prior art is seeking a solution to this problem, particularly given the economic demands that are being placed upon hospitals and medical facilities in reducing the high cost of health care.

OBJECTS AND SUMMARY OF THE INVENTION

The present invention is directed to providing a medical storage assembly for reusable medical equipment and includes a washable main utility storage bag, for example, made from nylon, of approximately a cylindrical configuration having an upper opening, a closed bottom and a surrounding interconnecting wall. This medical utility bag can be suspended from a mounting member in the form of a D-shaped bag holder ring or band made from stainless steel with a hinged lid closure. Attached to the utility bag holder ring is a mounting bracket that permits the mounting member to be mounted to any upright pole in the operating room such as an IV pole, the stainless steel leg of a surgical table, or even a storage or recharge pump cart that may be already existing within the operating room environment. Thus, the operating personnel can position the storage utility bag at a precise location that is needed without taking up any additional floor space.

A hinged lid closure member is also formed from a stainless steel material and can be a rigid flat structure configured to close the opening of the storage bag. Its upper surface is flat and can further function as a writing surface to permit the medical personnel to appropriately fill out patient forms corresponding with related disposal items. For example, plasma bags must be correlated with a particular patient and a patient form should be filled out and travel with the plasma bag. The flat closure lid facilitates this record-keeping procedure.

In one form of the present invention, the main storage bag will have a plurality of sub-storage bags removably mounted within the main storage bag so that different types of equipment can be stored in the same main storage bag. For example, an anesthesia laryngeal mask airway could be deposited within the main storage bag to reside at the bottom, while laryngoscope blades, laryngoscopes and other reusable equipment, could be deposited in the sub-storage bags for storage.

The main storage bag can have an interior fastener band, for example, made of a nap or hook material of a type commercially sold under the trademark VELCRO®. The corresponding sub-storage bags can have a complimentary fastening strip that permits their removable suspension from the internal wall of the main storage bag. Additionally, the sub-storage bags can include additional nap and hook fasteners to permit an interconnection between the sub-storage bags to hold them in internal open positions for receiving their designated items. The sub-storage bags can also have closure tabs, for example, of a nap and hook material to close the sub-storage bags when they are removed from the main storage bag.

The main storage bag can further have a series of eyelets for engagement with appropriate hooks on the mounting member with a drawstring extending about the perimeter of a tubular compartment that surrounds the opening of the main storage bag so that the medical personnel can pull the drawstring which will also perform the simultaneous operation of removing the eyelet openers from the hooks and pulling the main storage bag off of its mounting member for removing the main storage bag from the operating room.

An alternative embodiment of the present invention can use the same mounting member with a different storage bag which is designed to secure and store the blood and transfusion product plastic containers such as plasma bags and the required accompanying paperwork for return to the clinical laboratory's blood bank department or section. In this regard, the storage bag can include one or more exterior smaller bags permanently suspended on the outside of the main storage bag with an opening of a dimension to receive the paperwork, usually required in quadruplet copies, that are necessary to be filled out and transported with the used blood and transfusion product containers. Accordingly, a safe transport of these blood and transfusion product bags can be returned to the blood bank with the blood products paperwork appropriately stored so that the paperwork can be retrieved for recording of the vital signs, time, and date of transfusion and other blood bank required information, including patient specific data. The mounting member's pivoting lid can also provide a convenient writing surface for the easy recording of this required blood bank information.

BRIEF DESCRIPTION OF THE DRAWINGS

FIG. 2 is a cross-sectional view taken along the lines 2—2 of FIG. 1;

FIG. 4 is a front perspective view of a sub-storage bag;

FIG. 5 is a rear perspective view of a sub-storage bag of FIG. 4;

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide a medical storage assembly for reusable medical equipment.

Figure 1:
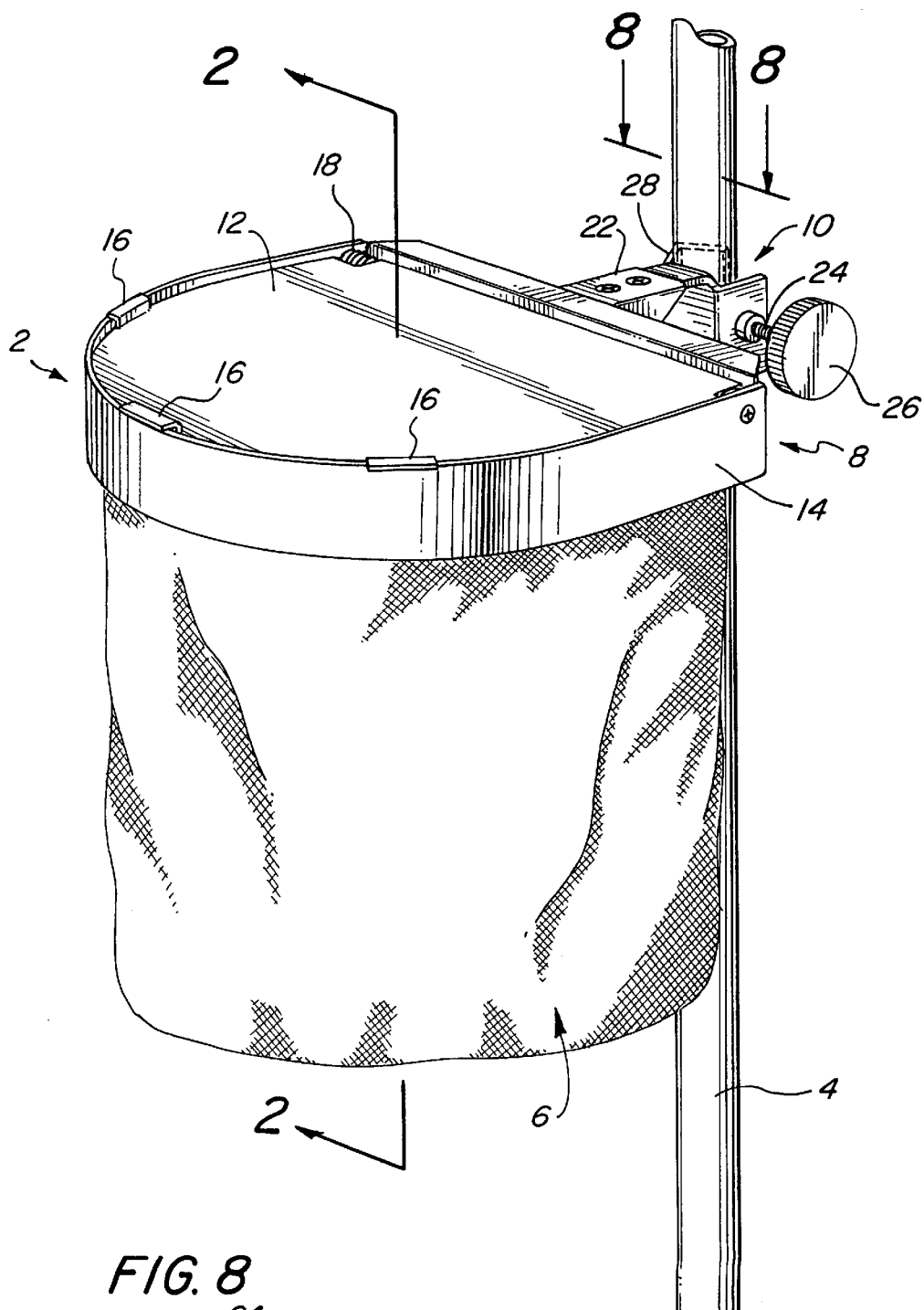
FIG. 1 is a perspective view of the medical storage assembly of the present invention in a first embodiment.

Referring to FIG. 1, a medical storage assembly 2 is shown mounted on a vertical pole 4 such as an IV pole that is frequently used in an operating room. The medical storage assembly 2 includes a main storage bag 6 and a mounting member 8 which can secure the main storage bag 6 in an operative upright position. A mounting bracket assembly 10 can be removably mounted to a vertical support member or an IV pole 4. A flat movable lid member 12 is connected to the mounting member or support member 8 and is configured to close the opening of the main storage bag 6 as shown in FIG. 1. The main storage bag 6 can be formed from a washable material such as nylon or other material consistent with the reusable medical products that are to be stored. The specific characteristics of the main storage bag 6 will be discussed further with the other views.

Figure 7:
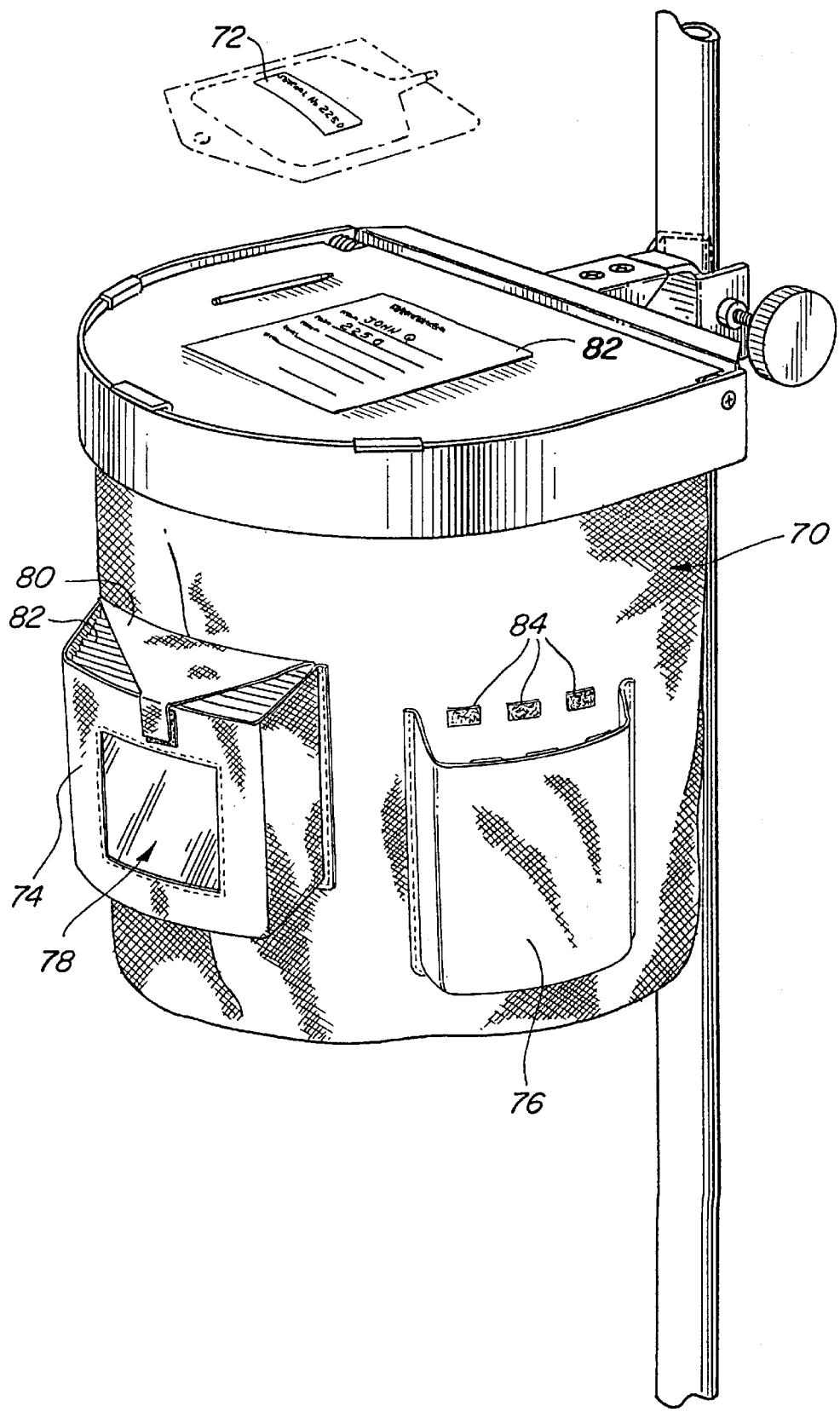
FIG. 7 is a front perspective view of another embodiment of the present invention.

The mounting or support member 8 basically comprises a band member 14 of stainless steel having a substantially "D" shaped configuration. The lid member 12 is also formed of a thin stainless steel plate and is configured to be closed within the "D" perimeter of the band member 14. A series of L-shaped stop members 16 are spaced about the lid member 14 and are dimensioned to rest upon the upper edge of the band member 14. Thus, in this first embodiment, the lid member 12 is recessed from the upper surface of the band member 14 to provide a roll-off resistant tabletop surface. As can be seen in FIG. 7, the lid member 12 can also serve the function of a writing surface for filling out appropriate medical forms related with the medical items stored within the main storage bag 6. The lid member 12 is mounted through a hinge assembly to the mounting or support member 8. A pair of springs 18, one on each side of the shaft 20, are designed to exert a sufficient force to hold the lid member 12 at any position between an open and close position. As shown in FIG. 2, the spring energy or force generated by the springs 18 at either side of the shaft 20 create a sufficient friction force to counterbalance the weight of the lid member 12. Thus, the medical personnel in the operating room can position the lid member 12 in an open position without fear that it will fall and create a disturbing sound. Additionally, the same medical personnel can lower the lid member 12 to the position shown in FIG. 7 to use it as a convenient writing surface for required medical forms 82.

Figure 8:
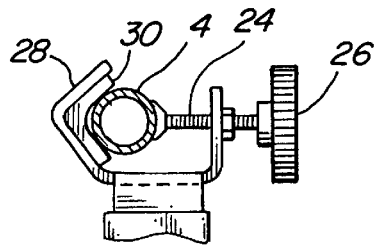
FIG. 8 is a plan view of a mounting bracket assembly.

A cantilevered arm 22 can mount the mounting bracket assembly 10 for connection with a support structure. Since the present design wishes to eliminate the necessity of an additional cart in the operating room, the mounting bracket assembly includes a vise structure as shown in FIG. 8. Thus, a threaded shaft with a concave end 24 is mounted within a threaded aperture so that a user can adjustably move the knob 26 for securing or releasing the vertical pole 4 in a holder member 28 which can include a resilient support pad 30. This vise arrangement permits an easy securement and release without marring the surfaces of the vertical support structure such as an IV pole, the leg of a surgical table, the leg of a storage or recharge pump cart, etc. As a result of this mounting bracketing assembly 10, the main storage bag 6 can be subjectively located or mounted at the precise location that is required without taking up any additional floor space.

Figure 3:
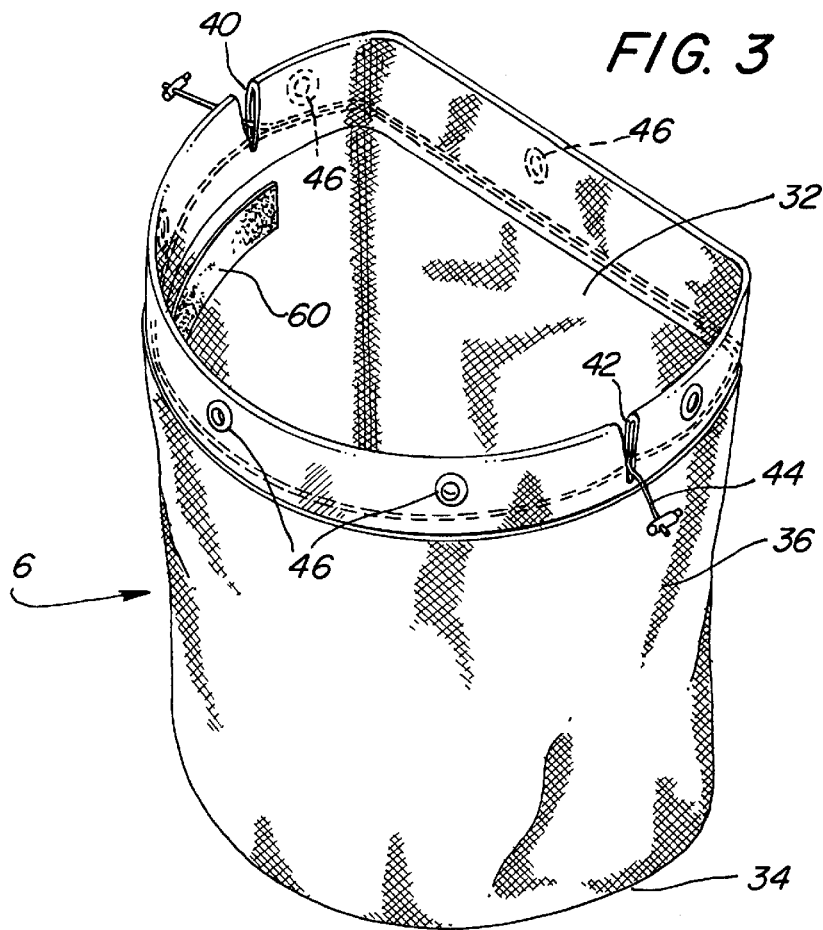
FIG. 3 is an upper perspective view of a main storage bag of the first embodiment.
Figure 6:
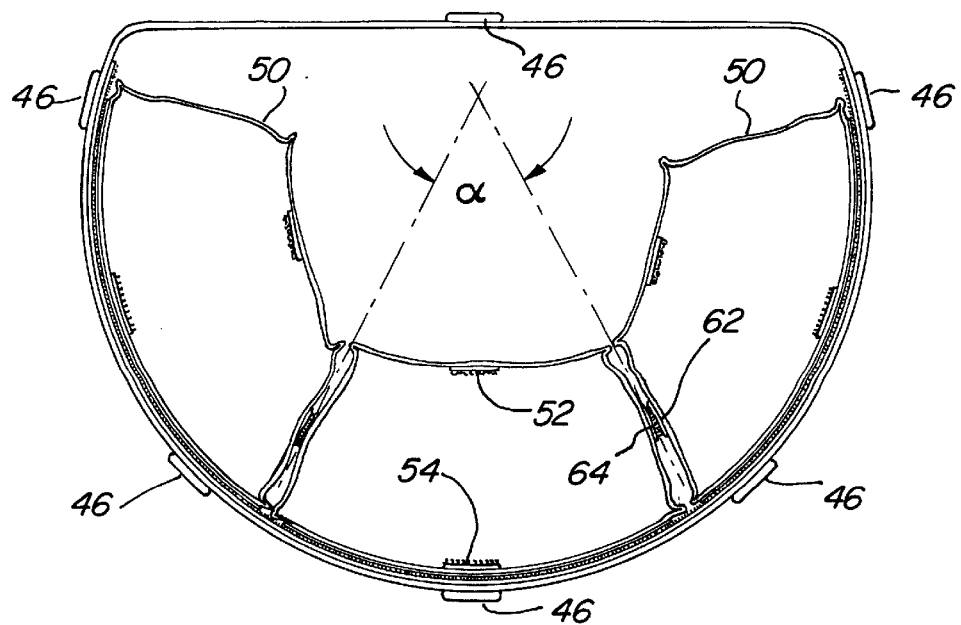
FIG. 6 is a plan view of the main storage bag and sub-storage bags of the first embodiment.

An example of a first embodiment of the main storage bag 6 can be seen in FIGS. 2, 3 and 6. The main storage bag 6 has an upper opening 32, a bottom 34 and an interconnecting wall 36. A closure assembly 38 extends about the opening 32 and comprises a tubular compartment that results from folding over the material of the storage bag and appropriately stitching or securing it into a closed cylindrical configuration. A pair of slits 40 and 42 provide an egress for the pegged ends of an elongated drawstring 44.

Spaced around the perimeter of the closure assembly 38 are a series of eyelets 46 which are designed, as seen in FIG. 2, to be operatively mounted onto hooks or tabs 48 which extend upward at an angle from an interior lower sides of the mounting member band 14. The relative placement and engagement between the opening of the eyelets 46 and the hooks 48 are sufficient to operatively suspend the main storage bag 6 for receipt of reusable medical equipment. The medical personnel, however, by grasping the pegged ends of the drawstring 44 and pulling upon the pegs not only close the opening 32 of the main storage bag 6, but further releases the main storage bag 6 from its suspension engagement with the hooks 48 on the mounting member 8. Thus, a fast and efficient manner of both releasing the main storage bag 6 and securing the contents of the main storage bag 6 is provided. The removed main storage bag 6 is then subsequently taken from the operating room to the appropriate department for reconditioning as reusable medical equipment.

In the first embodiment of the present invention, an auxiliary feature of a plurality of sub-storage bags 50 can also be mounted for suspension within the internal cavity of the main storage bag 6. The sub-storage bags 50 can be seen in FIGS. 4 and 5 with a plan view shown in FIG. 6. The opening of each of the sub-storage bags 50 is approximately a truncated sector of a circle or alternatively can be described as an opening that encompasses an area generally defined by concentric arcs of a common angle a as shown in FIG. 6. The sub-storage bags 50 are also stitched to be of a hardy construction and can be formed from a nylon or other appropriate material. A pair of fastener tabs 52 and 54 can be mounted within the internal upper side walls of each sub-storage bag 50 to permit an individual closing of each bag. Thus, a hook and nap material can be utilized which is commercially available under the trademark VELCRO®. The rear side wall 56 can support a strip or band of a fastening material 58 for engagement with a complimentary fastening band 60 that is mounted on the interior interconnecting wall 36 of the main storage bag 6. Again, the fastening material 58 and 60 can be of the nap and hook configurations that was mentioned above.

To provide additional support structure for maintaining the openings of the sub-storage bags 50, complimentary fastening tabs 62 and 64 can be used to interconnect adjacent side walls of the sub-storage bags 50 to provide additional rigidity and strength in maintaining an open operative position as shown in FIG. 6. Thus, the sub-storage bags 50 can be removably mounted within the main storage bag 6 and when filled, can also be removed with the opening of the sub-storage bag 50 closed by the fastener tabs 52 and 54.

Thus, as seen in FIG. 2, laryngeal mask airways 66 can be deposited within the main storage bag 6, while plastic laryngoscope blades 68 can be stored in one of the sub-storage bags 50. When the operation is finished, or the main storage bag 6 is filled, the medical personnel cleaning the operating room can grasp the pegged ends of the drawstring 44 and, by pulling them, he/she can release the eyelets 46 from the hooks 48, while simultaneously closing the opening 32 of the main storage bag 6. The large inside closure pockets or sub-storage bags 50 provide a readily available compact and protected storage location. This not only protects the supplies and the reusable medical equipment, but also protects the operating room personnel from contaminating themselves, while the remaining space within the main storage bag 6 can be used as a convenient depository for other reusable medical items such as the laryngeal mask airways 66.

With regards to the positioning of the hook material, it is preferred that the nap or fiber gripping surface be sewn on the inside fastening material 60 of the main storage bag 6 with the hook material being positioned on the fastening material 58 of the sub-storage bags 50. The liberal amount of material used for the respective bands permits the sub-storage bags 50 to be easily mounted without close inspection for alignment and the hook material will not come into contact with the back of the medical personnel's hands when they deposit reusable equipment into the main storage bag 6, thereby reducing the chance of possible scratching or breaking either the skin or surgical glove of the medical personnel.

A second embodiment of the present invention is disclosed in FIG. 7 wherein a main storage bag 70 can be mounted on the same mounting bracket assembly 10 that was used in the first embodiment of the present invention. The main storage bag 70 is particularly adapted to store blood and transfusion products such as plasma bags and to also associate directly the transfusion use paperwork that is routinely issued for patient use by the clinical laboratory's blood bank department or section. As can be expected, it is extremely important that a traceability be provided between the specific blood product that has been injected into a patient and the patient's identity. This embodiment permits a compact storage and protection (from inadvertent discarding and/or damage or contamination of the blood and blood products on the floor), while providing a safe transport of the blood and transfusion product bags back to the blood bank. The lid member 12 provides a convenient work surface for filling out the necessary paperwork that must be stored and retrieved for recording the vital signs, time, date of transfusion and other blood bank required information, including a patient's specific data. Generally, in an operating environment, contaminated transfusion product bags have been frequently placed on any readily available surface within the reach of the anesthesiologist or other operating room surgical personnel once the items have been used, or in emergency situations, they are frequently dropped onto the floor. Additionally, the necessary blood bank transfusion paperwork can accumulate on the anesthesia machine work surface or on the anesthesia cart. As a result, it is quite possible that the small transfusion slips 82 are not properly completed and they are either misplaced, or worse, they are discarded with the contaminated material at the end of the surgical procedure. Frequently, the blood bank transfusion product bags shown schematically as item number 72 may be contaminated from being co-mingled with other discarded contaminated products from the surgery and are frequently returned to the blood bank in a plastic bag, often with other body fluid contaminated items, including body parts, or may even be mixed with blood bank transfusion product bags from other surgeries. They also may be inadvertently discarded with the other disposable metal, plastic and paper items at the end of the surgical procedure.

To resolve this problem, the main storage bag 70 can include one or more external compartments 74 and 76. As shown in FIG. 7, the external compartment 74 can be of a configuration to receive transfusion slips which are usually in quadruplicate form and a clear plastic vision panel 78 can be provided to insure that there are slips positioned within the compartment 74. A lid with an appropriate fastener tab can be used to close the external compartment 74 so that the medical slips 82 are firmly kept with the transfusion blood products. Usually, the medical slips 82 must be initially filled out to confirm compatibility with the particular blood type of the patient, before use of the transfusion blood product, and then subsequent information must be added at a later time period after the use of the transfusion blood product, e.g., condition of patient, reactions, etc. External compartment 74 provides a convenient storage compartment for the medical slips that are not completely filled out, while the lid member 12 insures a convenient writing surface. The external compartment 76 can be used to store the completed medical slips 82. External compartment 76 can also have fastener tabs 84 to permit the closing of this external compartment.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A storage assembly for reusable medical equipment comprising:

a main storage bag having an opening, a bottom an interconnecting wall, and a fastener band extending across a portion of an inside of the interconnecting wall;

a plurality of sub-storage bags removably mounted within the main storage bag, the sub-storage bags including complimentary fastener bands for fastening to the main storage bag fastener band and to each others thereby being removably connected together to provide open configurations for receiving medical equipment.

a mounting member for securing the main storage bag in an operative upright position;

means for removably mounting the mounting member about a supporting vertical pole to permit the storage bag to be operatively suspended from the mounting member; and a rigid flat movable lid member connected to the mounting member and configured to enable the closing of the opening of the storage bag.

2. The storage assembly of claim 1 wherein the mounting member is a metallic band having a D-shaped opening for suspending the main storage bag.

3. The storage assembly of claim 1 wherein an opening of each sub-storage bag is a truncated sector of a circle.

4. The storage assembly of claim 1 wherein the fastener band and the complimentary fastener bands are made of a nap and hook material.

5. A storage assembly for reusable medical equipment comprising:

a main storage bag having an opening, a bottom and an interconnecting wall;

a mounting member for securing the main storage bag in an operative upright position;

means for removably mounting the mounting member about a supporting vertical pole to permit the storage bag to be operatively suspended from the mounting member;

a rigid flat movable lid member connected to the mounting member and configured to enable the closing of the opening of the storage bag, and p1 an exterior small bag of a dimension for receiving and holding written patient information forms relative to the used medical equipment stored in the main storage bag to enable a coordination of a patient with specific medical equipment.

6. A medical storage bag for receiving and storing a plurality of different reusable medical items comprising:

a main storage bag having an opening, a bottom and an interconnecting wall;

a plurality of sub-storage bags having an opening, a bottom and an interconnecting wall of smaller size than the main storage bag;

fastener means for removably mounting and suspending the sub-storage bag on an interior portion of the interconnecting wall, the fastener means including a fastener band extending across a portion of an inside of the interconnecting wall, wherein the sub-storage bags include complimentary exterior fastener bands for fastening to the main storage bag fastener band and means for removably interconnecting the sub-storage bags to each other to maintain their respective openings to be held in a predetermined open position whereby the main storage bag and the respective sub-storage bags can receive and store different medical items.

7. The medical bag of claim 6 wherein the fastener band and the complimentary fastener bands are made of one of a nap and hook material.

8. The medical storage bag of claim 6 wherein the opening of each sub-storage bag is a truncated sector of a circle.

9. The medical storage bag of claim 6 wherein the opening of each sub-storage bag encompasses an area generally defined by concentric arcs of a common angle.

10. The medical storage bag of claim 6 wherein each sub-storage bag includes an interior fastener means to interconnect two sides of the wall together.

11. A storage assembly for storing a plurality of reusable medical equipment items comprising:

a main storage bag having an opening, a bottom and an interconnecting wall;

a closure assembly is mounted about the opening and includes a pull member for closing and holding closed the main storage bag opening for transportation;

a plurality of sub-storage bags are removably mounted for suspension within the main storage bag, each sub-storage bag includes an opening, a bottom and a plurality of sides extending between the opening and the bottom, at least one side on each sub-storage bag is removably interconnected to another side of an adjacent sub-storage bag to maintain their respective openings in an operative position for receiving medical equipment items;

a metallic support member is removably mounted to the main storage bag for suspending the main storage bag and the plurality of sub-storage bags in operative positions;

a mounting bracket assembly is connected to the support member and is adapted for removable securement to a vertical support member; and a rigid flat movable lid member is connected to the support member and is configured to close the opening of the main storage bag whereby the main storage bag is suspended from the metallic support member for receiving and segregating a plurality of reusable medical equipment items, a user can release the main storage bag from the metallic support member and activate the closure assembly to permit transportation of the reusable medical equipment items and the installing of a replacement main storage bag on the mounting bracket assembly.

12. The storage assembly of claim 11 wherein the closure assembly includes a tubular space about the opening of the main storage bag with a plurality of exterior openings and the metallic support member includes a plurality of hooks appropriately spaced for removably engaging the exterior openings to suspend the main storage bag.

13. The storage assembly of claim 12 wherein the metallic support member is a stainless steel band formed into substantially a D-shaped opening.

14. The storage assembly of claim 13 wherein the rigid flat movable lid member is mounted by a spring pivot assembly that permits the lid member to be held at any desired position from open to close.

15. The storage assembly of claim 14 wherein the mounting bracket assembly includes a vise member for engaging a support structure between a resilient support member.

16. A medical storage bag for receiving and storing a plurality of different reusable medical items comprising:

a main storage bag having an opening, a bottom and an interconnecting wall;

a plurality of sub-storage bags having an opening, a bottom and an interconnecting wall of smaller size than the main storage bag, the opening of each sub-storage bag forming a truncated sector of a circle;

fastener means for removably mounting and suspending the sub-storage bag on an interior portion of the interconnecting wall; and means for removably interconnecting the sub-storage bags to each other to maintain their respective openings to be held in a predetermined open position whereby the main storage bag and the respective sub-storage bags can receive and store different medical items.

17. A medical storage bag for receiving and storing a plurality of different reusable medical items comprising:

a main storage bag having an opening, a bottom and an interconnecting wall;

a plurality of sub-storage bags having an opening, a bottom and an interconnecting wall of smaller size than the main storage bag, the opening of each sub-storage bag encompassing an area generally defined by concentric arcs of a common angle;

fastener means for removably mounting and suspending the sub-storage bag on an interior portion of the interconnecting wall; and means for removably interconnecting the sub-storage bags to each other to maintain their respective openings to be held in a predetermined open position whereby the main storage bag and the respective sub-storage bags can receive and store different medical items.

18. A medical storage bag for receiving and storing a plurality of different reusable medical items comprising:

a main storage bag having an opening, a bottom and an interconnecting wall;

a plurality of sub-storage bags having an opening, a bottom and an interconnecting wall of smaller size than the main storage bag;

fastener means for removably mounting and suspending the sub-storage bag on an interior portion of the interconnecting wall; and means for removably interconnecting the sub-storage bags to each other to maintain their respective openings to be held in a predetermined open position whereby the main storage bag and the respective sub-storage bags can receive and store different medical items, wherein each sub-storage bag includes an interior fastener means to interconnect two sides of the wall together.

* * * * *